United States Patent
Fu et al.

(10) Patent No.: US 12,227,752 B1
(45) Date of Patent: Feb. 18, 2025

(54) **USE OF MTNAC33 GENE AND AN ENCODED PROTEIN THEREBY IN IMPROVING THE BIOMASS AND DROUGHT TOLERANCE OF *MEDICAGO SATIVA* L.**

(71) Applicants: QINGDAO INSTITUTE OF BIOENERGY AND BIOPROCESS TECHNOLOGY, CHINESE ACADEMY OF SCIENCES, Qingdao (CN); Inner Mongolia Pratacultural Technology Innovation Center Co. Ltd, Hohhot (CN)

(72) Inventors: Chunxiang Fu, Qingdao (CN); Ruijuan Yang, Qingdao (CN); Wenwen Liu, Qingdao (CN); Zhaoming Wang, Qingdao (CN); Feng Yuan, Qingdao (CN); Ying Sun, Qingdao (CN); Shiqie Bai, Qingdao (CN); Chuanen Zhou, Qingdao (CN); Jiajun Yan, Qingdao (CN); Yaling Liu, Qingdao (CN); Xiaowei Zhang, Qingdao (CN); Shanshan Jiang, Qingdao (CN)

(73) Assignees: QINGDAO INSTITUTE OF BIOENERGY AND BIOPROCESS TECHNOLOGY, CHINESE ACADEMY OF SCIENCES, Qingdao (CN); Inner Mongolia Pratacultural Technology Innovation Center Co. Ltd, Hohhot (CN)

( * ) Notice: Subject to any disclaimer, the term of this patent is extended or adjusted under 35 U.S.C. 154(b) by 0 days.

(21) Appl. No.: 18/783,627

(22) Filed: Jul. 25, 2024

(51) Int. Cl.
*C12N 15/82* (2006.01)
*A01H 1/04* (2006.01)

(52) U.S. Cl.
CPC ........... *C12N 15/8273* (2013.01); *A01H 1/04* (2013.01); *C12N 15/8205* (2013.01)

(58) Field of Classification Search
None
See application file for complete search history.

(56) References Cited

FOREIGN PATENT DOCUMENTS

| CN | 111518186 A | * | 8/2020 |
| CN | 117264966 A | * | 12/2023 |

OTHER PUBLICATIONS

Uniprot Accession G7JBJ4, 2022, uniprot.org/uniprotkb/G7JBJ4/ entry (Year: 2022).*
European Nucleotide Archive Accession JR546871, 2012, ebi.ac.uk/ena/browser/view/JR546871). (Year: 2012).*
NAC domain class transcription factor [Medicago truncatula] Jun. 8, 2014.
Roles of NAC transcription factors in the regulation of biotic and abiotic stress responses in plants Sep. 3, 2013.

* cited by examiner

*Primary Examiner* — Brent T Page
*Assistant Examiner* — Aleksandar Radosavljevic
(74) *Attorney, Agent, or Firm* — JEEN IP LAW, LLC

(57) ABSTRACT

The present invention relates to the use of MtNAC33 gene and a protein encoded thereby in the cultivation of high-biomass and drought-tolerant alfalfa, belonging to the technical field of plant genetic engineering. The plant protein encoded by MtNAC33 gene has the amino acid sequence set forth in SEQ ID NO: 2, and MtNAC33 gene has the nucleotide sequence set forth in SEQ ID NO: 1. In the present invention, the drought tolerance of *Arabidopsis thaliana* and alfalfa can be significantly improved by regulating the expression level of MtNAC33 in alfalfa. The phenotypes of delayed flowering, increased leaf-to-stem ratio and more biomass in alfalfa were also developed, which has an important effect for genetic improvement of stress resistance and biomass of forage grass and other crops.

3 Claims, 18 Drawing Sheets

Specification includes a Sequence Listing.

```
                              SEQUENCE LISTING

Sequence total quantity: 12
SEQ ID NO: 1            moltype = DNA  length = 1074
FEATURE                 Location/Qualifiers
source                  1..1074
                        mol_type = genomic DNA
                        organism = Medicago truncatula
SEQUENCE: 1
atggccgaaa caaaattgat gattccaggg tttcgttttc accccactga tgttgagctg  60
gtaatgtatt ttctcaagag gaagattttg ggtagaaaat tccctttaa tgtcattgat  120
gaacttgaca tttacaagta tgctccatgg gatctaccag aaaaatcttt gctcaagagt  180
ggtgatttgc aatggtactt ctttaccct gtcggaaaga aatatgcac gggaggagg  240
atgaatcgga caacagaagt aggctactgg aagactacag ggaaggatag gtcgattgaa  300
cataggaatc aagtggtggg gatgataaga accctggtgt tcacactgg caaagctcct  360
aaaggagacc gaactgattg ggttatgcat gaatacagac ttgaaaacaa agacctagct  420
gacaatggtg ttccacagaa ctcctatgtg atttgtagg tatttcaaaa ggaaggtcct  480
ggtcccagga atggtgcaca gtatggaaaa ccatttaatg agaaagactg ggatagcgaa  540
gaggaaattg attatgtaca agctgtccct gttgctgctg tgtctgcacc agctctcatt  600
ctacctagct caagccatat ttctgaagaa atgatatgc atacctctgc aagggggatgc  660
actggacaga cctctttatc aggtctatca agattggcac cctctgcac gacacaccct  720
tcagctccag gcaatcaagc tgatgatgac attttatcca tgcttgctat ctttgacgat  780
gaaaatgcat tggctgggaa tgaaaacaat ggatctgaga aggtcgataa tcctggtcag  840
gcaaacaatg ctgaagatgt accttattta atttcaaatg agattttga ggacttggga  900
gatctcaaca gcttggttgg attagatgaa ggaggcggtt tttcctatgg ccaaaaagat  960
gagtacgaaa agctttctac tggcaacgtc tctttgtttt gcaaccccc tgatttcttt  1020
gagttgcttg acctagaggt gccattatct tggcagacta aacatgatgg ctga       1074

SEQ ID NO: 2            moltype = AA  length = 357
FEATURE                 Location/Qualifiers
source                  1..357
                        mol_type = protein
                        organism = Medicago truncatula
SEQUENCE: 2
MAETKLMIPG FRFHPTDVEL VMYFLKRKIL GRKFPFNVID ELDIYKYAPW DLPEKSLLKS  60
GDLQWYFFTP VGKKYCTGGR MNRATEVGYW KTTGKDRSIE HRNQVVGMIR TLVFHTGKAP  120
KGDRTDWVMH EYRLENKDLA DNGVPQNSYV ICRVFQKEGP GPRNGAQYGK PFNEKDWDSE  180
EEIDYVQAVP VAAVSAPALI LPSSSHISEE NDMHTSARGC TGQTSLSGLS RLMPSGTTHP  240
SAPGNQADDD ILSMLAIFDD ENALAGNENN GSEKVDNPGQ ANNAEDVPYL ISNEIFEDLG  300
DLNSLVGLDE GGGFSYGQKD EYEKLSTGNV SLFCNPPDFF ELLDLEVPLS WQTKHDG    357

SEQ ID NO: 3            moltype = DNA  length = 37
FEATURE                 Location/Qualifiers
source                  1..37
                        mol_type = other DNA
                        organism = synthetic construct
SEQUENCE: 3
tccttcaccc gggatccatg gccgaaacaa aattgat                           37

SEQ ID NO: 4            moltype = DNA  length = 37
FEATURE                 Location/Qualifiers
source                  1..37
                        mol_type = other DNA
                        organism = synthetic construct
SEQUENCE: 4
acccttttatc gggatcctca gccatcatgt ttagtct                          37

SEQ ID NO: 5            moltype = DNA  length = 23
FEATURE                 Location/Qualifiers
source                  1..23
                        mol_type = other DNA
                        organism = synthetic construct
SEQUENCE: 5
ggtaacattg tgctcagtgg tgg                                          23

SEQ ID NO: 6            moltype = DNA  length = 23
FEATURE                 Location/Qualifiers
source                  1..23
                        mol_type = other DNA
                        organism = synthetic construct
```

```
SEQUENCE: 6
aacgacctta atcttcatgc tgc                                          23

SEQ ID NO: 7            moltype = DNA  length = 20
FEATURE                 Location/Qualifiers
source                  1..20
                        mol_type = other DNA
                        organism = synthetic construct
SEQUENCE: 7
aaagactggg atagcgaaga                                              20

SEQ ID NO: 8            moltype = DNA  length = 18
FEATURE                 Location/Qualifiers
source                  1..18
                        mol_type = other DNA
                        organism = synthetic construct
SEQUENCE: 8
cctggagctg aagggtgt                                                18

SEQ ID NO: 9            moltype = DNA  length = 20
FEATURE                 Location/Qualifiers
source                  1..20
                        mol_type = other DNA
                        organism = synthetic construct
SEQUENCE: 9
cccactggat gtctgtaggt                                              20

SEQ ID NO: 10           moltype = DNA  length = 21
FEATURE                 Location/Qualifiers
source                  1..21
                        mol_type = other DNA
                        organism = synthetic construct
SEQUENCE: 10
agaattaagt agcagcgcaa a                                            21

SEQ ID NO: 11           moltype = DNA  length = 20
FEATURE                 Location/Qualifiers
source                  1..20
                        mol_type = other DNA
                        organism = synthetic construct
SEQUENCE: 11
atttttgagg acttgggaga                                              20

SEQ ID NO: 12           moltype = DNA  length = 20
FEATURE                 Location/Qualifiers
source                  1..20
                        mol_type = other DNA
                        organism = synthetic construct
SEQUENCE: 12
ccagtagaaa gcctttcgta                                              20
```

USE OF MTNAC33 GENE AND AN ENCODED PROTEIN THEREBY IN IMPROVING THE BIOMASS AND DROUGHT TOLERANCE OF *MEDICAGO SATIVA* L.

CROSS-REFERENCE TO RELATED APPLICATION

This patent application claims the benefit and priority of Chinese Patent Application No. 202310959073.2 filed with the China National Intellectual Property Administration on Aug. 1, 2023, the disclosure of which is incorporated by reference herein in its entirety as part of the present application.

REFERENCE TO SEQUENCE LISTING

A computer readable XML file entitled "Use of MtNAC33 gene and an encoded protein thereby in IMPROVING THE BIOMASS AND drought TOLERANCE OF *Medicago sativa* L.-sequence listing", which was created on Nov. 13, 2024 with a file size of about 13,338 bytes, contains the sequence listing for this application, has been filed with this application, and is hereby incorporated by reference in its entirety.

TECHNICAL FIELD

The present disclosure belongs to the field of plant genetic engineering technology and specifically relates to the use of MtNAC33 gene and an encoded protein by MtNAC33 in cultivating high-biomass and drought-tolerant alfalfa.

BACKGROUND

Alfalfa (*Medicago sativa*. L) is globally cultivated as a paramount leguminous forage, earning the moniker "Queen of the forages" due to its richness in protein, vitamins, and fatty acids which are beneficial to both human and animals. In addition, alfalfa has a well-developed root system and shows strong resistance to abiotic stress. With the surge in livestock production, particularly in developing nations like China and dramatic change of global climate, the demand for new alfalfa varieties displays high quality and yield, enhanced resistance to drought and heat stress is becoming increasingly urgent. Genetic engineering is used to improve alfalfa quality, which can more quickly cultivate high-quality, high-yield, and enhanced-resistant alfalfa varieties, thereby promoting the development of husbandry.

Drought is a prevalent environmental stress in most regions of the world, and it limits the growth, development, and distribution of plants. About one-third of the world's area is arid and semi-arid. What's more, dramatic change of global climate makes drought stress more serious. Drought stress has caused a large reduction in forage production, seriously affecting agricultural development. In recent years, the research on strategies that plants response to drought resistance has gradually become the universal concern. Based on the principle of "not competing with the people for food, and not competing with crops for land", the planting of drought-tolerant/resistant forage grasses including genetic improvement in arid-alkali land will achieve the dual goals of saving arable land and improving the development of husbandry in arid-alkali areas.

Transcription factors (TFs) control the regulation of various genes and can usually achieve co-regulation of multiple traits. The NAC (NAM, ATAF and CUC) protein family is a plant-specific transcription factor superfamily that plays an important role in diverse developmental processes such as plant growth and development, metabolic regulation, and abiotic stress responses. Currently, among the researches on improving plant drought tolerance/resistance, most genes cannot meet the dual needs of drought tolerance/resistance and high yield at the same time. Therefore, our study provides a target for the biomass and drought tolerance genetic improvement and molecular breeding of perennial forage grasses and other crops.

SUMMARY OF THE DISCLOSURE

The first purpose of this present is to provide the use of the MtNAC33 gene and an encoded protein thereby in the cultivation of high-yield and drought-tolerant alfalfa to solve the problems of the lack of elite drought-resistant genes in current and failing to simultaneously meet the needs of molecular design for improving alfalfa biomass yield and drought tolerance.

The present disclosure achieves the goals through the following technical solutions.

The present disclosure provides the use of MtNAC33 gene in the cultivation of high-biomass and drought-tolerant alfalfa. The nucleotide sequence of MtNAC33 gene is shown in SEQ ID NO: 1.

The present disclosure also provides the use of a protein encoded by MtNAC33 gene in the cultivation of high-biomass and drought-tolerant alfalfa. The amino acid sequence of the protein is shown in SEQ ID NO: 2.

The present disclosure also provides the use of a recombinant vector of pEG100-MtNAC33 in the cultivation of high-biomass and drought-tolerant alfalfa. The recombinant vector of pEG100-MtNAC33 contains the MtNAC33 gene.

Further, the present disclosure includes construction of the pEG100-MtNAC33 vector; introducing MtNAC33 expression cassette into the plant by using an ultrasonic-assisted leaf disc transformation procedure mediated by an *Agrobacterium tumefaciens* strain EHA105; using DL-Phosphinothricin as the selection to obtain positive and overexpressing MtNAC33 alfalfa; wherein the transgenic plant shows more drought tolerance, delayed flowering time, increased leaf-to-stem ratio, and improved dry biomass.

The core features and inventive concepts of the present disclosure are the following:

In the present disclosure, genetic engineering is used to improve the expression level of MtNAC33 gene in the wild-type Zhongmu No. 1 alfalfa through an overexpressing transgenic technology, which can achieve significant results in a short time.

In the present disclosure, the traits and drought tolerance of transgenic alfalfa are analyzed.

Compared with the prior arts, the present disclosure has the following advantages:

In the present disclosure, the overexpression of MtNAC33 significantly delays the flowering time, improves the leaf size and leaf-to-stem ratio, increases the fresh and dry biomass yield of alfalfa, increases the contents of soluble proteins and monosaccharides and improves the forage quality of alfalfa.

In the present disclosure, the overexpression of MtNAC33 significantly represses the stomatal aperture and improves the drought tolerance of alfalfa.

The genetically improved plants obtained in the present disclosure may be integrated into conventional breeding projects thus providing new germplasm resources for the cultivation of leguminous forage.

BRIEF DESCRIPTION OF THE DRAWINGS

FIG. 6A-6C show a phenotype diagram of MtNAC33OE transgenic alfalfa and the wild-type Zhongmu No. 1 alfalfa (control); wherein FIG. 6A shows that MtNAC33OE lines displays delayed flowering time. FIG. 6B shows branches of the wild type and MtNAC33OE lines. FIG. 6C shows leaf sizes of the wild type and MtNAC33OE lines.

FIG. 8A-FIG. 8E show a phenotype of MtNAC33OE transgenic alfalfa and the wild-type Zhongmu No. 1 alfalfa (control, Ctrl) after drought treatment; wherein FIGS. 8A and 8B is a diagram showing the comparison of photosynthesis intensity of isolated leaves after 24, 48, and 72 hours, detected by plant fluorescence imaging instrument; FIG. 8C shows the phenotypes under 15-day drought treatment and after re-watered, bar=30 cm; and stomata number (FIG. 8D) and stomatal aperture (FIG. 8E) under drought stress. Values means±SE (n=3). One-way ANOVA (Dunnett's multiple-range test), *$p<0.01$. **$p<0.01$.

FIG. 9A-FIG. 9D are the analysis of forage quality in MtNAC33OE transgenic alfalfa and the wild-type Zhongmu No. 1 alfalfa; wherein FIG. 9A shows the monosaccharide content in each group, FIG. 9B shows the starch content in each group, FIG. 9C shows the water-soluble carbohydrate content in each group, and FIG. 9D shows the ratio of soluble protein to total protein in each group.

DETAILED DESCRIPTION OF THE EMBODIMENTS

The present disclosure will be described in further detail below with reference to the examples and drawings. Unless otherwise specified, all materials, reagents, and molecular marker probes used in the following examples can be commercially purchased by the applicant.

Example 1: Acquisition of Overexpressing MtNAC33 Transgenic *Arabidopsis thaliana*

The primers MtNAC33-OE-F and MtNAC33-OE-R were designed, using pENTR as the entry vector. The BamH I restriction site and the 9 bases following the restriction site were introduced at the end as the linker to obtain a full-length sequence of MtNAC33, which was used as a template. PCR amplification was performed using the above primers.

The primer sequences were as follows:

```
MtNAC33-OE-F:
                                    (SEQ ID NO: 3)
TCCTTCACCCGGGATCCATGGCCGAAACAAAATTGAT;
```

```
MtNAC33-OE-R:
                                    (SEQ ID NO: 4)
ACCCTTTATCGGGATCCTCAGCCATCATGTTTAGTCT.
```

The underlined bases were the homologous linker.

The PCR reaction system was: 2 µL cDNA, 5 µL 10×Buffer, 4 µL 2.5 mM dNTP, 1 µL (each) of 10 µM forward primer/reverse primer, 0.5 µL 5 U/µL Taq enzyme and 36.5 µL ddH$_2$O. The materials were added to a tube on ice and mixed well. PCR reaction conditions were: 94° C. for 5 minutes; 94° C. for 30 seconds, 56° C. for 45 seconds; 72° C. for 2 minutes, 34 cycles; and 72° C. for 10 minutes.

Figure 1:
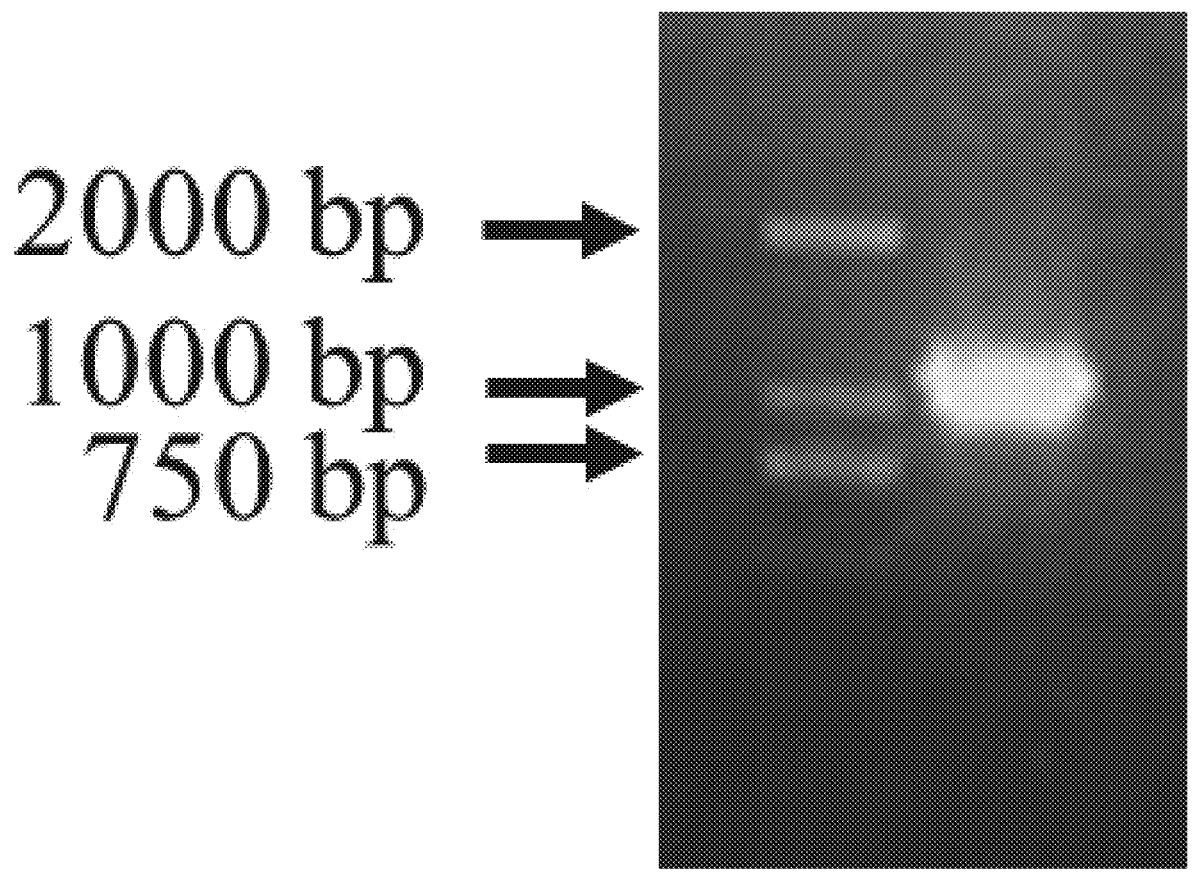
FIG. 1 shows the electrophoretogram illustrating the PCR amplification of MtNAC33 coding sequence from *Medicago truncatula*.
Figure 2:
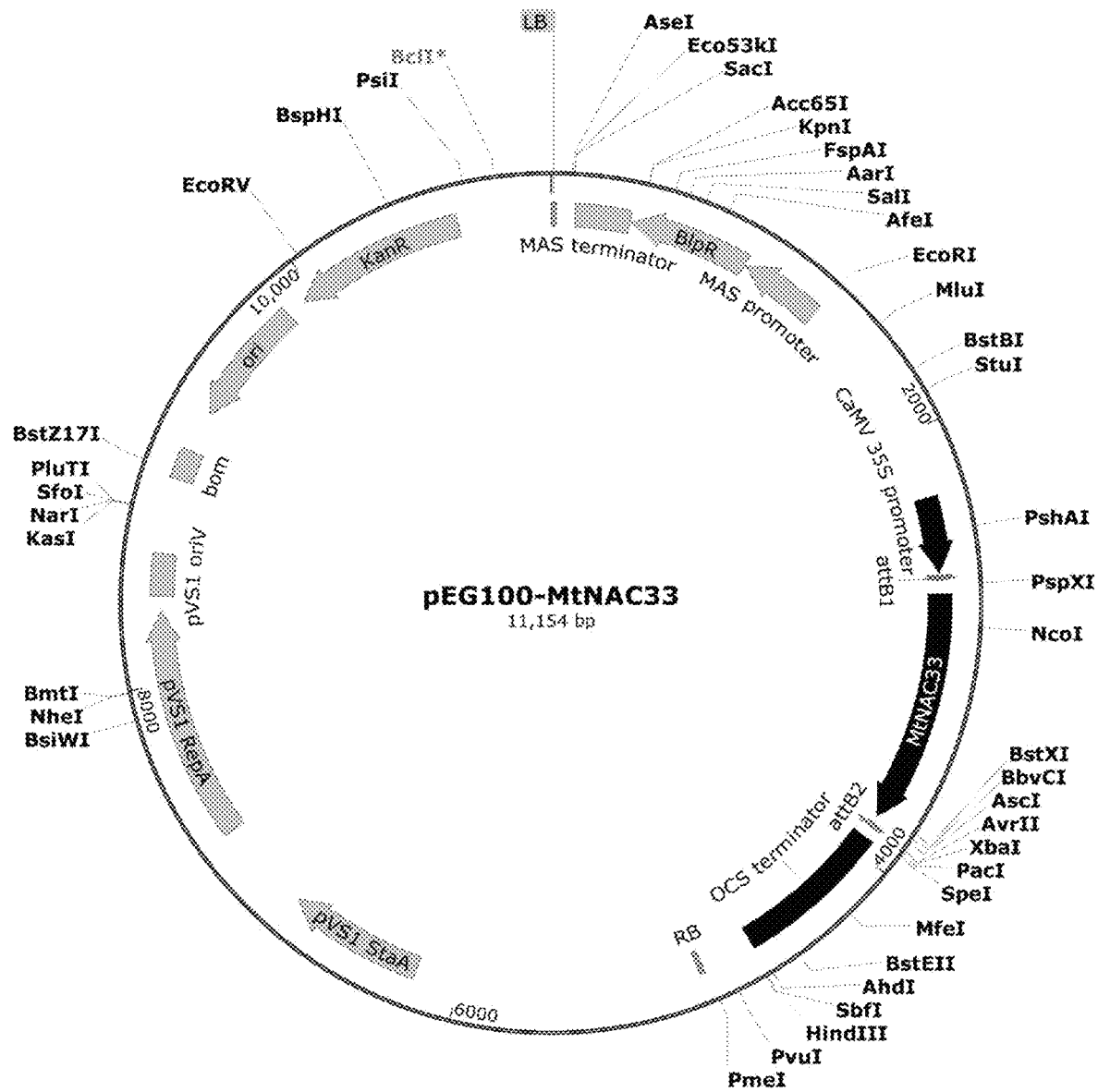
FIG. 2 is a schematic diagram of pEG100-harboring a 35S::MtNAC33 expression cassette.

The 1,074 bp fragments (FIG. 1) after amplification were recovered (using a Promega gel recovery kit) and conventionally sequenced (Beijing BGI Genomics Co., Ltd.). The pENTR vector was digested with restriction endonuclease BamH I and recovered. The above two fragments were litigated and transfected into *E. coli* to obtain positive clones of the entry recombinant vector and the plasmid was extracted. EcoR V endonuclease was used for digestion at 37° C. for 1 h, and the target fragments were finally recombined into the pEG100 vector using Gateway technology (FIG. 2). The recombination reaction system was as follows: 100 ng enzyme digestion recovery fragments, 50 ng pEG100 vector plasmid, 1 µL LR enzyme (Invitrogen, product catalog number 11791020), and water was made up to 10 µL. The reaction system was incubated at 25° C. for 6 h. Then the reaction mixture was transfected into *E. coli* and a positive-recombinant-bacteria plasmid pEG100-MtNAC33 with the correct sequence was obtained, and the positive recombinant bacteria plasmid pEG100-MtNAC33 was transfected into *Agrobacterium tumefaciens* strain EHA105.

The obtained EHA105 containing pEG100-MtNAC33 plasmid was inoculated into 200 mL YEP culture medium (containing 50 mg/L kanamycin and 50 mg/L rifampicin) and cultured overnight. The cells were collected and centrifuged at 4,000 rpm for 10 min at room temperature, and the cells were diluted to OD$_{600}$ of 0.9-1.1 using MS liquid culture medium containing 10% sucrose and 0.03% Silwet L-77. *Arabidopsis thaliana* (Col-0) was transfected using the flower dip method. After soaking the flowers for one minute each time and repeating two times, the plants were shaded with a black plastic bag for 24 hours and then cultured normally. The T$_0$ generation seeds were collected and positive plants were screened using 50 µg/L glufosinate ammonium in MS0 medium. The T$_1$ generation was the seeds and plants produced by self-pollination of the T$_0$ generation, and the T$_3$ generation was the seeds and plants produced by self-pollination of the T$_2$ generation. The transgenic plants of MtNAC33OE_A and MtNAC33OE_C screened from the positive T$_3$ generation plants were used as homozygous transgenic plants after identification of the over-expression levels of MtNAC33.

Homozygous transgenic plants were selected, and total RNA from leaves was extracted using the TriZol Reagent kit (Invitrogen, Catalog No. 15596026). The content and purity of total RNA were detected by agarose gel electrophoresis and using a nucleic acid analyzer (NanoDrop). 1.0 µg of total RNA was used for reverse transcription reaction, and reverse transcriptase (Promega, Catalog No. M1701) was used to reverse-transcribed the RNA into cDNA following the user Manual. qRT-PCR detection was conducted using the above-obtained cDNA as a template and primers MtNAC33-ORF-QF and MtNAC33-ORF-QR, with the *Arabidopsis thaliana* Actin gene used as the internal reference gene. The primer sequences were as follows:

```
AtActin-F:
                                  (SEQ ID NO: 5)
GGTAACATTGTGCTCAGTGGTGG;

AtActin-R:
                                  (SEQ ID NO: 6)
AACGACCTTAATCTTCATGCTGC;

MtNAC33-ORF-QF:
                                  (SEQ ID NO: 7)
AAAGACTGGGATAGCGAAGA;

MtNAC33-ORF-QR:
                                  (SEQ ID NO: 8)
CCTGGAGCTGAAGGGTGT.
```

Figure 3:
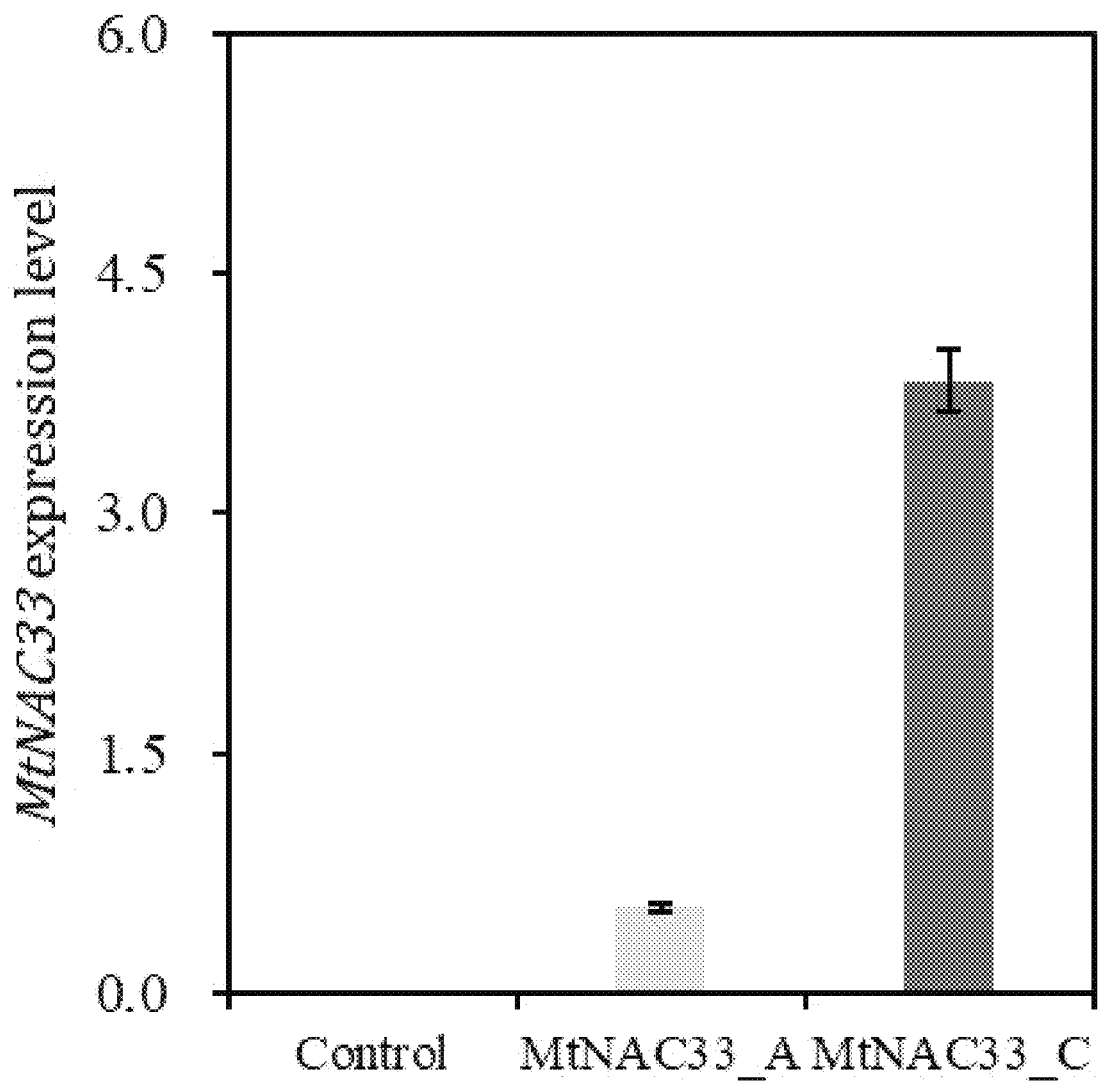
FIG. 3 shows the quantitative real-time PCR (qRT-PCR) results of MtNAC33 gene in different MtNAC33 overexpressing (MtNAC33OE) transgenic lines (MtNAC33OE_A and MtNAC33OE_C) and the wild-type *Arabidopsis thaliana* (control).

The qRT-PCR reaction system had a volume of 20 μL, including 1 μL (each) of forward primer/reverse primer, 2 μL of cDNA template, 10 μL of SYBR Green qRT Master Mix (Takara Biotechnology Co., Ltd.), and 6 μL of PCR-grade $H_2O$. The two-step reaction procedure was performed using Roche480. The test results showed that the expression levels of MtNAC33 in the transgenic plants MtNAC33OE_A and MtNAC33OE_C were significantly increased compared with that of the wild-type Col-0 (FIG. 3).

Example 2: Drought Tolerance of MtNAC33 Over-Expressing Transgenic *Arabidopsis thaliana*

Figure 4:
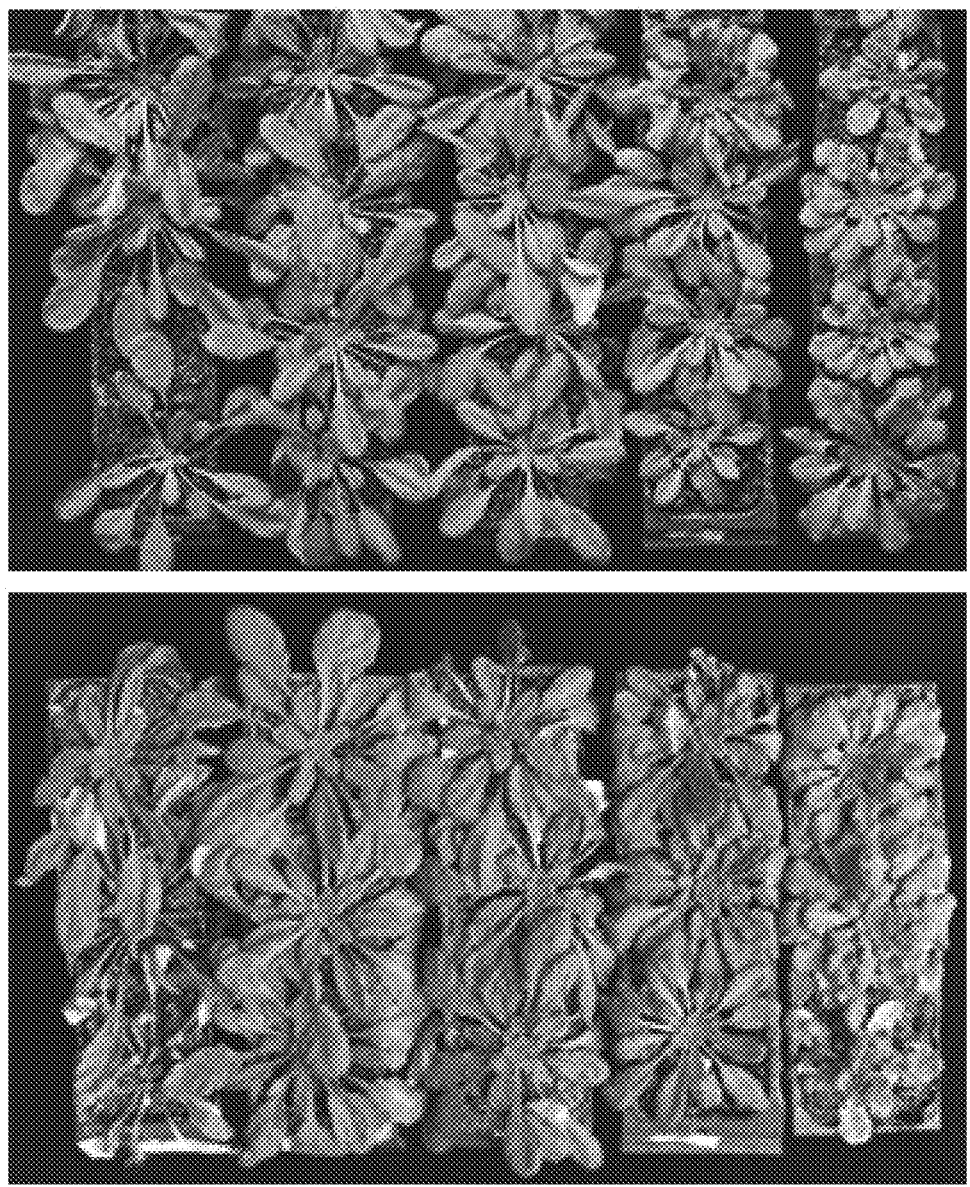
FIG. 4 shows the phenotypes of MtNAC33OE transgenic plants and the wild-type *Arabidopsis thaliana* (Col-0) after drought stress treatment.

The $T_3$ transgenic MtNAC33OE_A and MtNAC33OE_C *Arabidopsis*, which showed upregulated expression of MtNAC33 by quantitative PCR analysis in Example 1, were used as experimental lines and subjected to drought tests together with the wild type. One-month-old plants were cultivated under the same conditions were treated with normal watering (FIG. 4, the upper part) and no watering (FIG. 4, the lower part). After 10 days, the overexpression plants showed significant drought tolerance compared with that of the wild-type plants (FIG. 4).

In summary, by using the above transgenic method, overexpression of MtNAC33 in *Arabidopsis* can significantly enhance the drought tolerance of the plants.

The formula of 20×N6 vit was as follows:
$MgSO_4 \cdot 7H_2O$ 3.70 g/L
$KNO_3$ 56.60 g/L
$(NH_4)_2SO_4$ 9.26 g/L
$KH_2PO_4$ 8 g/L
The formula of 100×$CaCl_2$ was as follows:
100×$CaCl_2$ 6.3 g/500 ml
The formula of 200×NaFeEDTA was as follows:
NaFeEDTA 3.73 g/500 ml
The formula of 1000×SH was as follows:
$MnSO_4 \cdot H_2O$ 1 g/L
$H_3BO_3$ 500 mg/L
$ZnSO_4 \cdot 7H_2O$ 100 mg/L
KI 100 mg/L
$Na2MoO_4 \cdot 2H_2O$ 10 mg/L
$CuSO_4 \cdot 5H_2O$ 20 mg/L
$CoCl_2 \cdot 6H_2O$ 10 mg/L The formula of 1000×SH vit was as follows:
Nicotinic acid 500 mg/L
VB1 500 mg/L
VB6 500 mg/L
The formula of SH3a liquid culture medium was as follows:
N6 bulk (20×) 50 mL
$CaCl_2$ (100×) 10 mL
SH (1000×) 1 mL
Fe salt (200×) 5 mL
SH Vit (1000×) 1 mL
Inositol 0.1 g
Sucrose 30 g
2,4-D (2 mg/ml) 2 mL
6-BA (1 mg/ml) 0.5 mL
The formula of SH3a solid culture medium was as follows:
N6 bulk (20×) 50 mL
$CaCl_2$ (100×) 10 mL
SH (1000×) 1 mL
Fe salt (200×) 5 mL
SH Vit (1000×) 1 mL
Inositol 0.1 g
Sucrose 30 g
2,4-D (2 mg/ml) 2 mL
6-BA (1 mg/ml) 0.5 mL
Phytagel 4 g
The formula of MSBK culture medium was as follows:
MS powder 4.43 g
Sucrose 30 g
6-BA (1 mg/mL) 0.5 mL
KT (2 mg/mL) 1 mL
Agar 7.8 g
The formula of SH9 culture medium was as follows:
N6 bulk (20×) 50 mL
$CaCl_2$ (100×) 10 mL
SH (1000×) 1 mL
Fe salt (200×) 5 mL
SH Vit (1000×) 1 mL
Inositol 0.1 g
Sucrose 30 g
Agar 7.5 g Example 3: Generation of Over-Expressing MtNAC33 Transgenic Alfalfa Plants The *Agrobacterium* EHA105 transfected with the recombinant plasmid of pEG100-MtNAC33 obtained in Example 2 was inoculated into 50 mL YEP culture medium (containing 50 mg/L kanamycin and 50 mg/L rifampicin) and cultured overnight until $OD_{600}$ of *Agrobacterium* EHA105 was 0.6-0.8. The cells were collected and centrifuged at 4,000 rpm for 10 min at room temperature. The *Agrobacterium* cells were resuspended in SH3a liquid culture medium containing 200 M acetosyringone, incubated at 280 for 2 h, and finally diluted to a bacterial solution with $OD_{600}$ of 0.2-0.3. Fresh young leaves of alfalfa were picked and sterilized with 0.5-1% sodium hypochlorite (NaClO) supplemented with 0.1% Tween 20 at room temperature for 8-10 min. The surface-sterilized leaves were poured into the stock *Agrobacterium* EHA105 bacterial solution. The leaves and Agrobacteria were sonicated in a SCIENT Z SB-120DT Ultrasonic Cleaner (40 kHz, 120 W) for 15 min at 15-20° C. Subsequently, they were co-cultivated in SH3a solid medium containing 100 μM acetosyringone for 24 to 48 hours in the dark at 22° C. The leaves were transferred onto SH3a solid medium containing 2 mg L DL-Phosphinothricin (PhytoTechnology Laboratories) and 300 mg L$^{-1}$ Timentin (Caisson, USA). Resistant calli were generated and proliferated for 4 to 6 weeks on MSBK culture medium containing 1 mg L$^{-1}$ DL-Phosphinothricin and 300 mg L$^{-1}$ Timentin. After the occurrence of green buds, transferred them to the SH9 culture medium containing 1 mg L$^{-1}$ DL-Phosphinothricin and 300 mg L$^{-1}$ Timentin, and rooted.

Fully developed leaf tissues of the transgenic and wild-type alfalfa plants were taken, and the total RNA samples of the plants were extracted and reverse-transcribed according to the method in Example 1 to obtain cDNA. Realtime fluorescence quantitative PCR detections of MtNAC33 were performed using the primer of MtNAC33-QF and MtNAC33-QR, with the alfalfa MsActin gene used as the internal reference gene. The primer sequences were as follows:

```
MsActin-F:
                         (SEQ ID NO: 9)
CCCACTGGATGTCTGTAGGT;

MsActin-R:
                         (SEQ ID NO: 10)
AGAATTAAGTAGCAGCGCAAA.

MtNAC33-QF:
                         (SEQ ID NO: 11)
ATTTTTGAGGACTTGGGAGA;

MtNAC33-QR:
                         (SEQ ID NO: 12)
CCAGTAGAAAGCCTTTCGTA.
```

Figure 5:
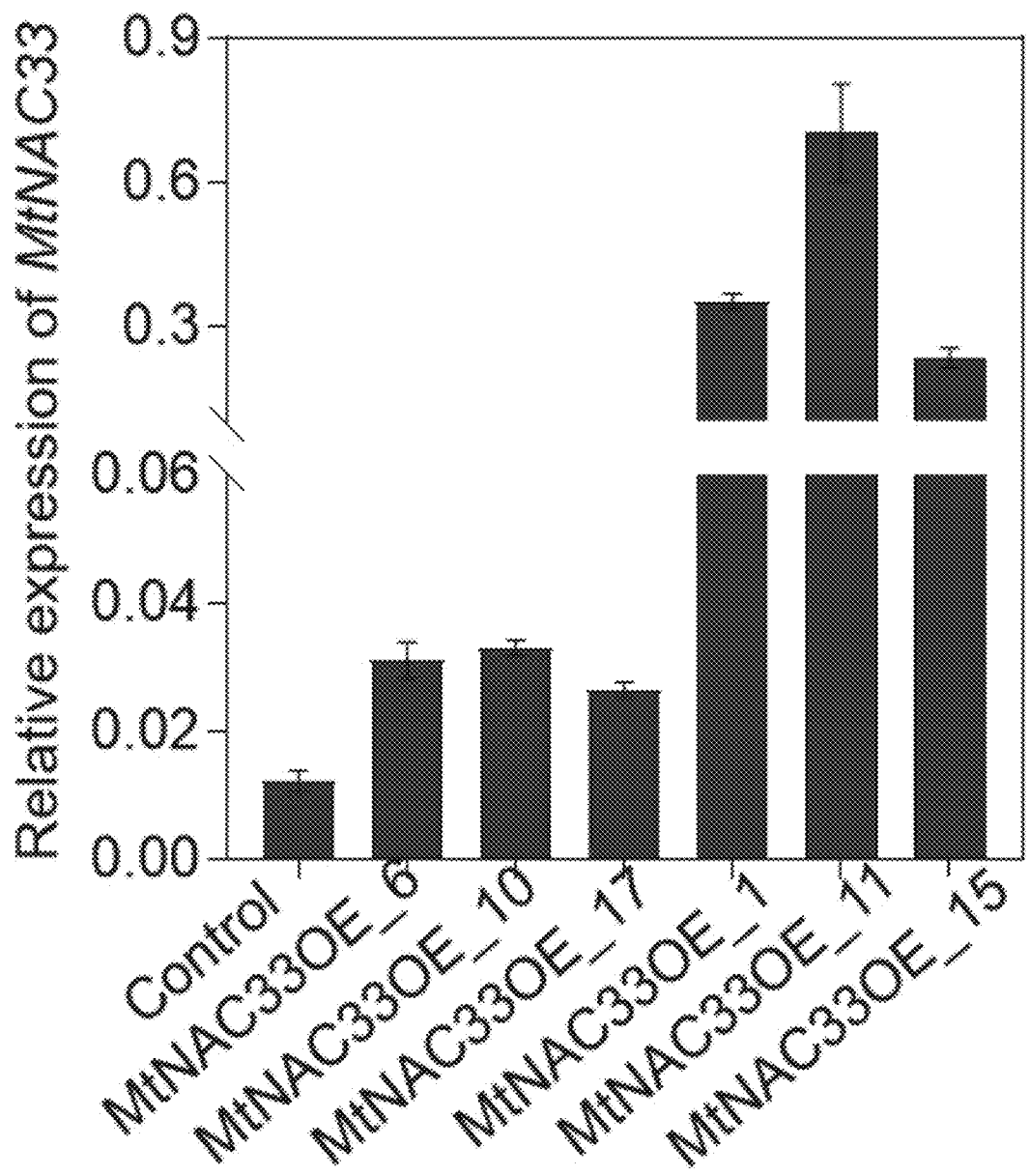
FIG. 5 shows the qRT-PCR results of MtNAC33 gene in NAC33 overexpressing (MtNAC33OE) transgenic alfalfa and the wild-type Zhongmu No. 1 alfalfa (control).
Figure 6A:
Figure 6B:
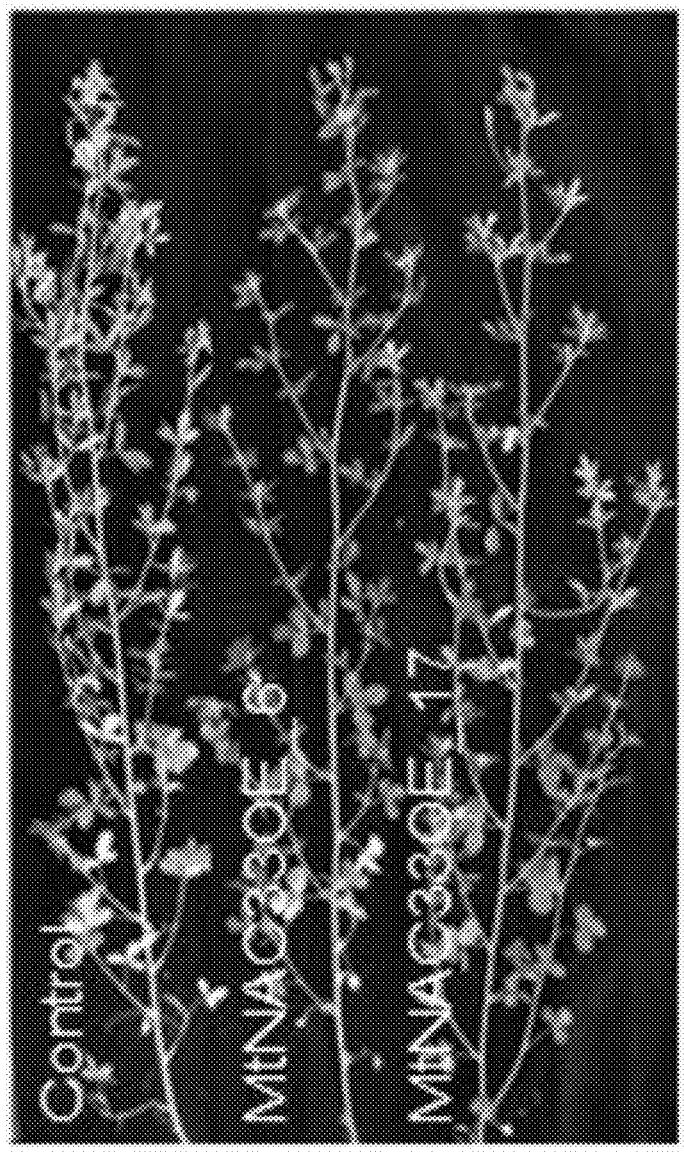
Figure 6C:
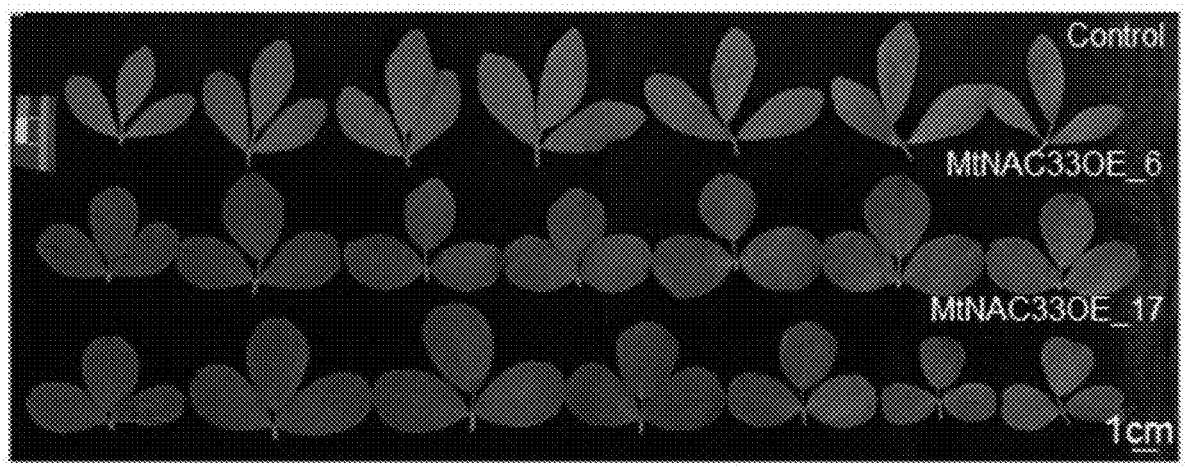
Figure 7:
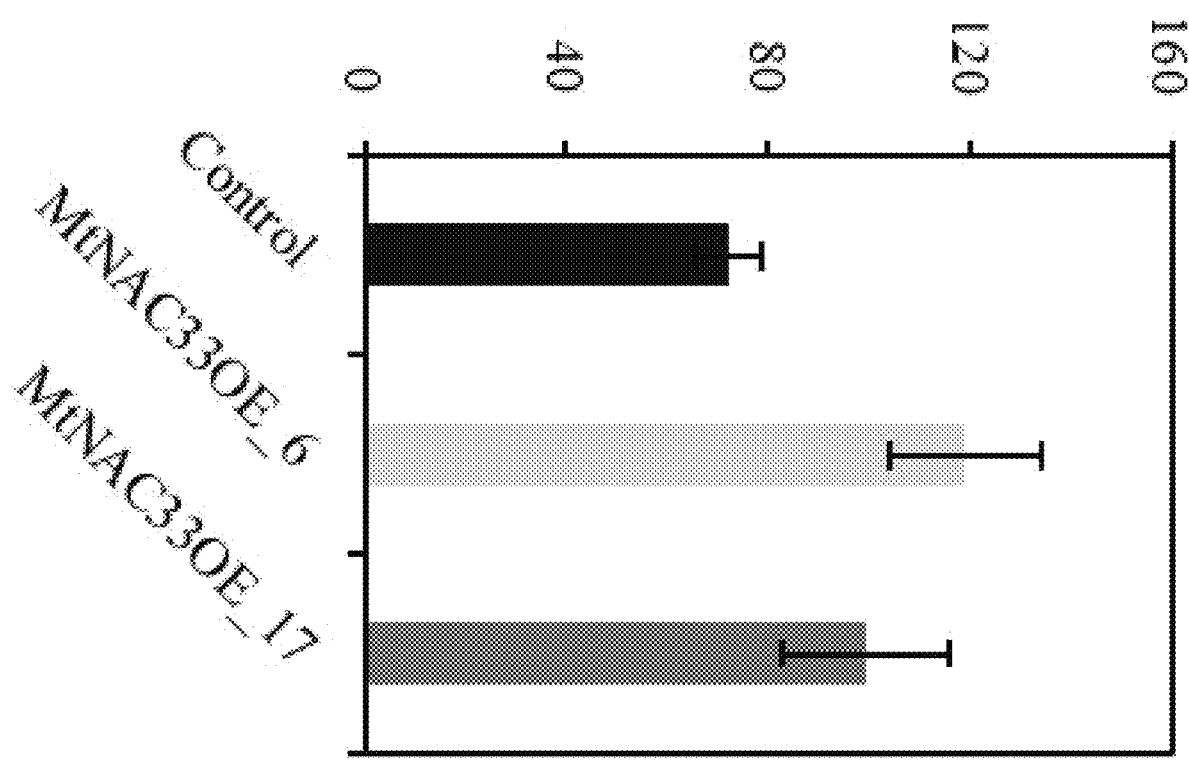
FIG. 7 shows the biomass of NAC33OE transgenic alfalfa and the wild-type Zhongmu No. 1 alfalfa (control).

The reaction system and method for qRT-PCR were the same as in Example 2. The results showed that the expression levels of MtNAC33 in the MtNAC33OE_6/17 lines were significantly increased compared with that of the wild-type alfalfa (FIG. 5).

Example 4: Phenotypes of Over-Expressing MtNAC33 Transgenic Alfalfa Plants

The transgenic plants, which showed over expression of MtNAC33 by qRT-PCR analysis in Example 3, were grouped based on their expression levels and corresponding phenotypes. The results showed that during the transgenic process, about 50% of the transgenic plants expressed 2-5 times of MtNAC33 transcripts than that of the wild-type plants (MtNAC33OE_1/6/10/11/15/17). The results showed that the transgenic plants had larger leaves, delayed flowering time, increased leaf-to-stem ratio, and more dry biomass at the early flowering stage (FIGS. 6A-6C and FIG. 7).

Figure 8A:
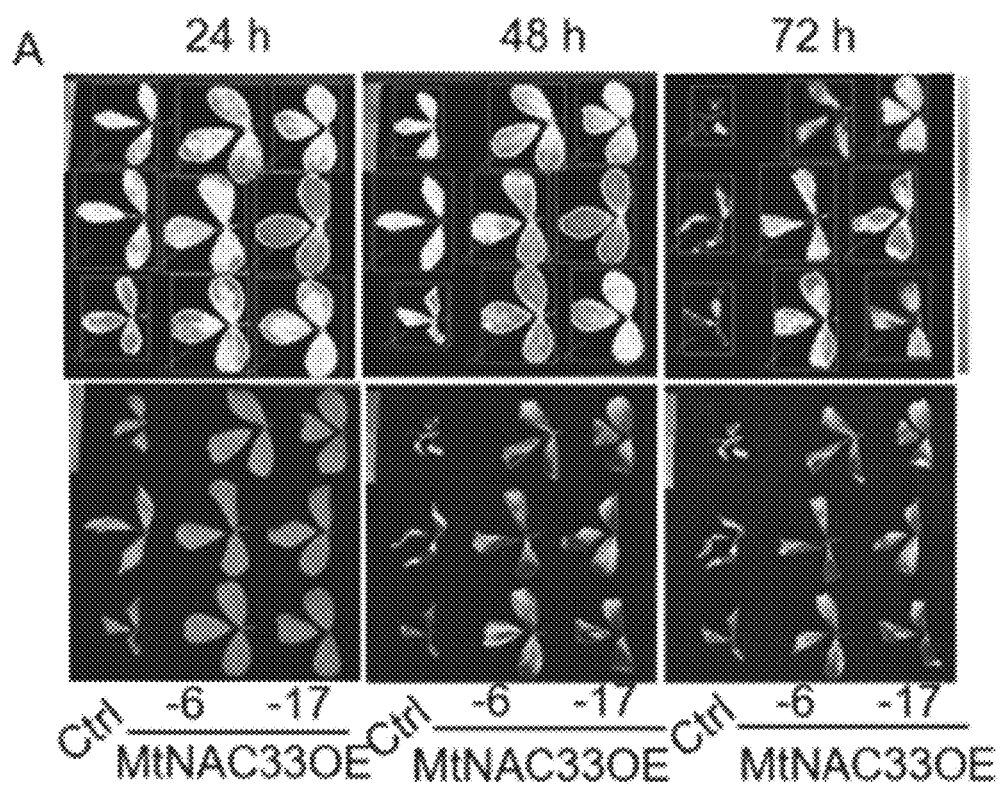
Figure 8B:
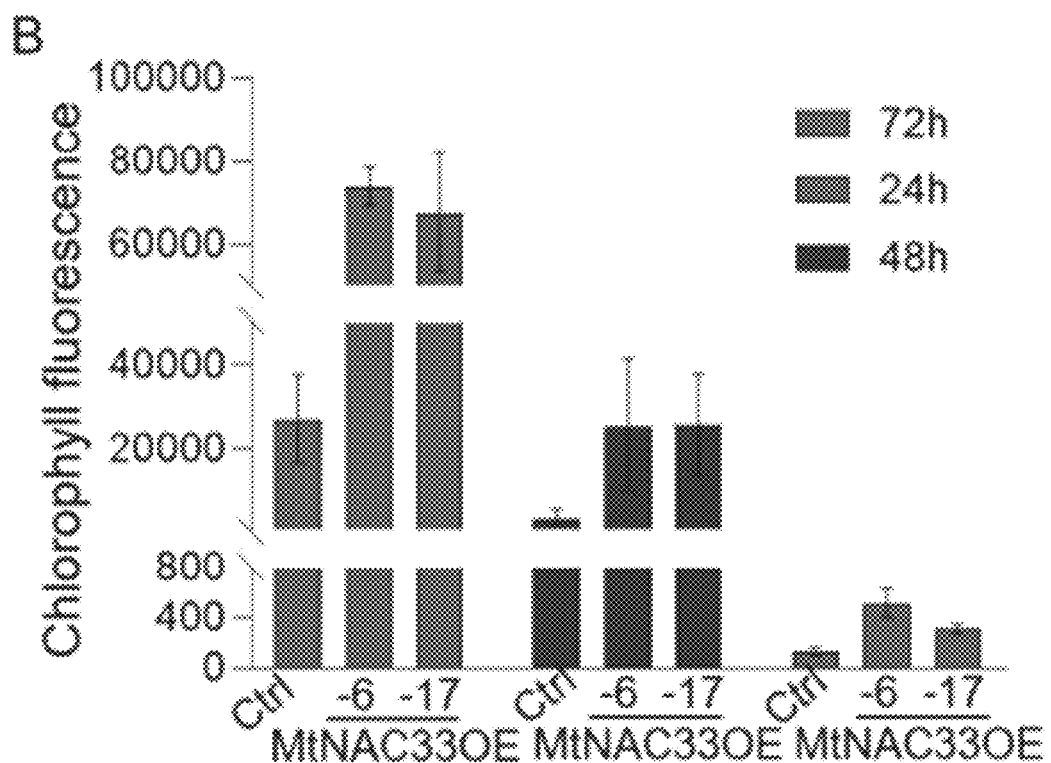
Figure 8C:
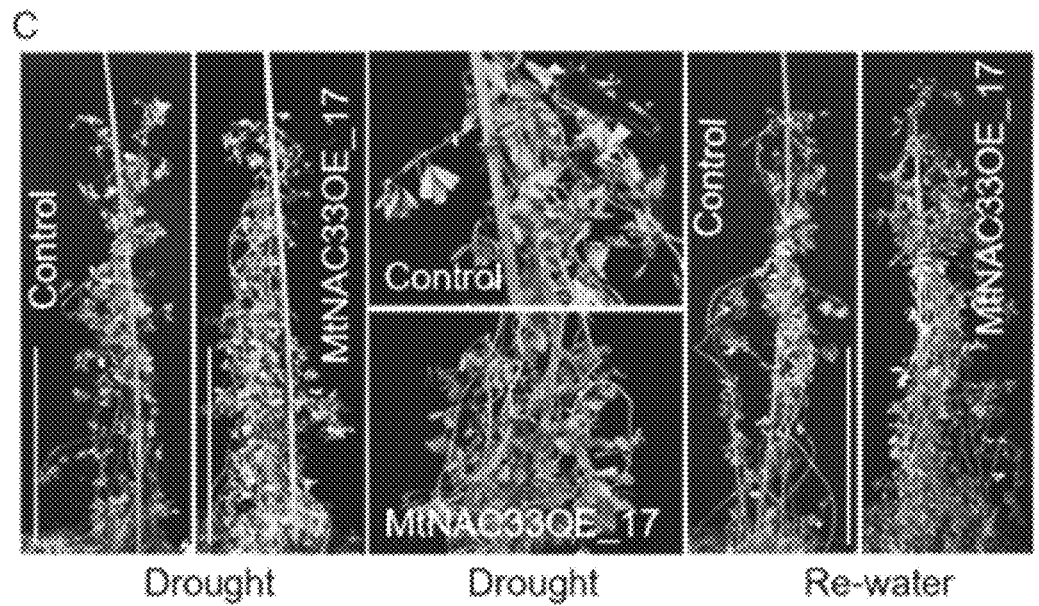
Figure 8D:
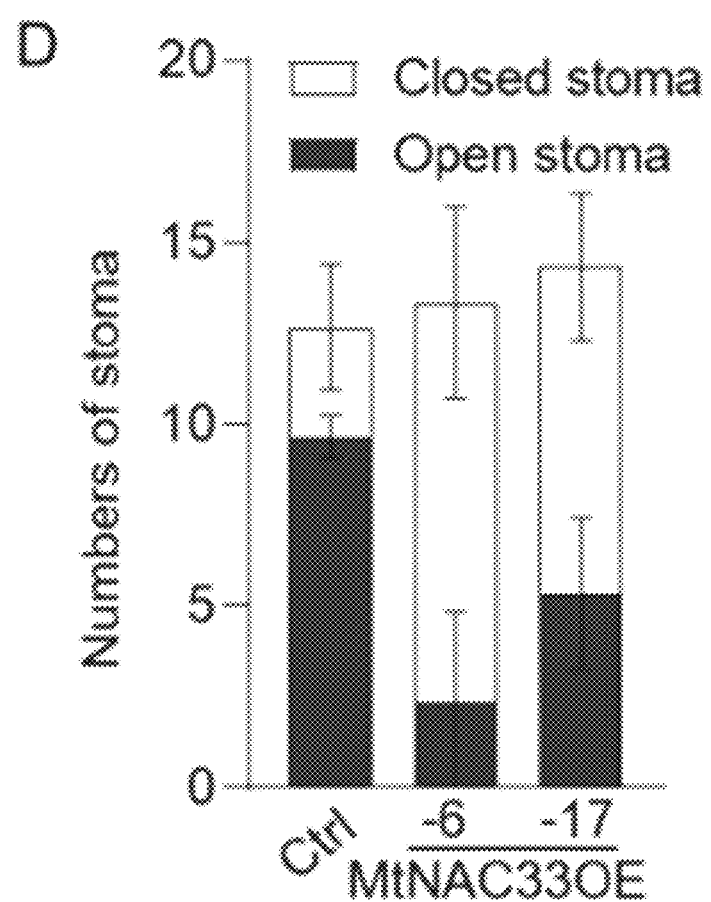
Figure 8E:
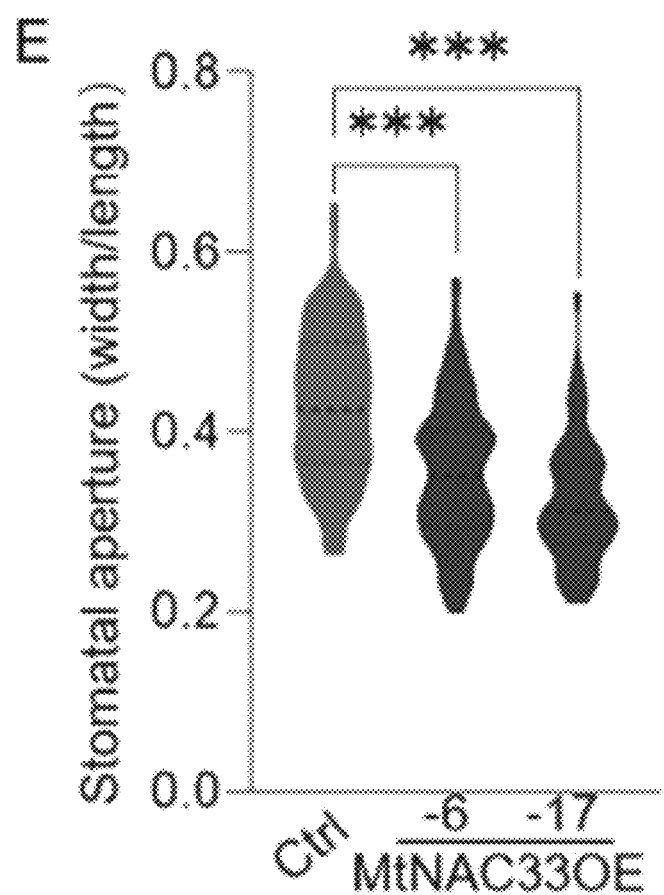
Figure 9A:
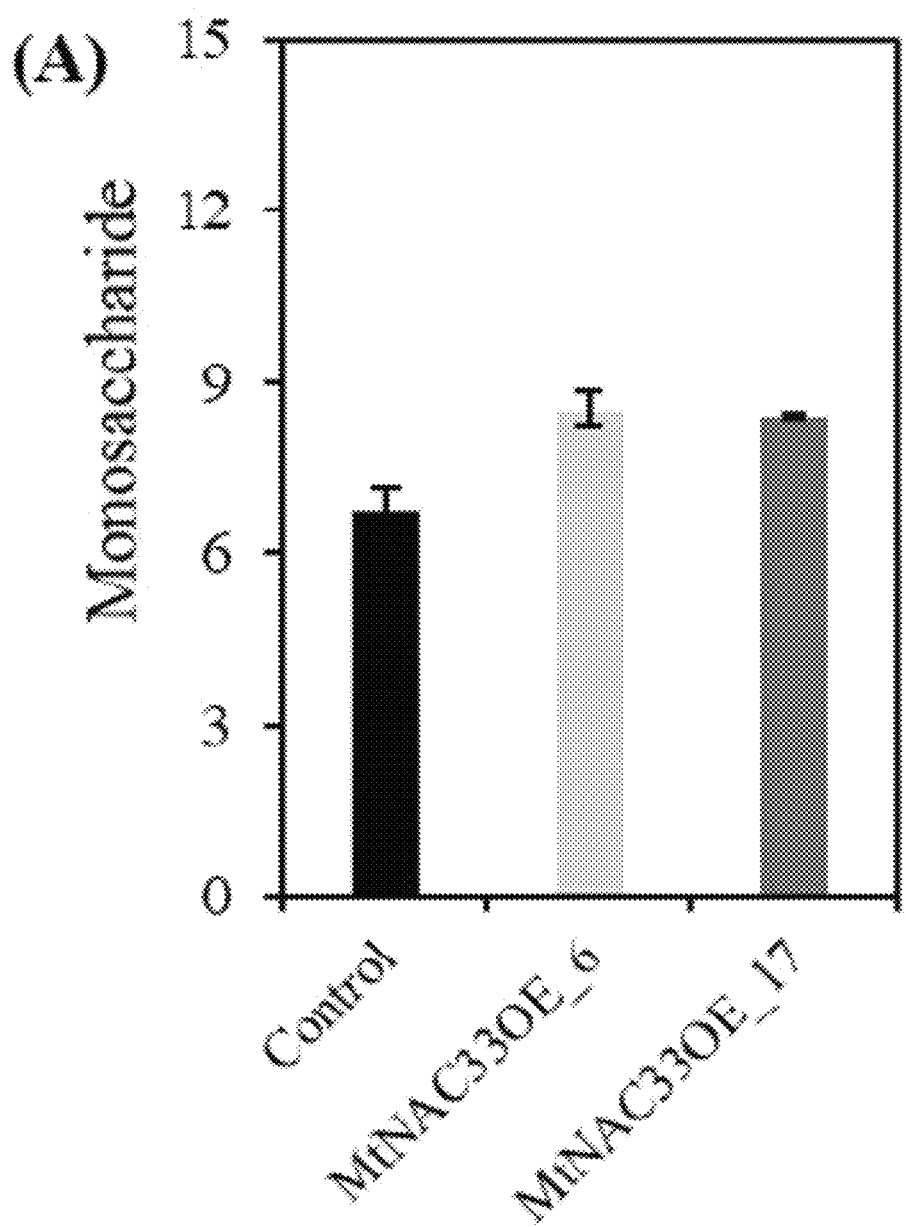
Figure 9B:
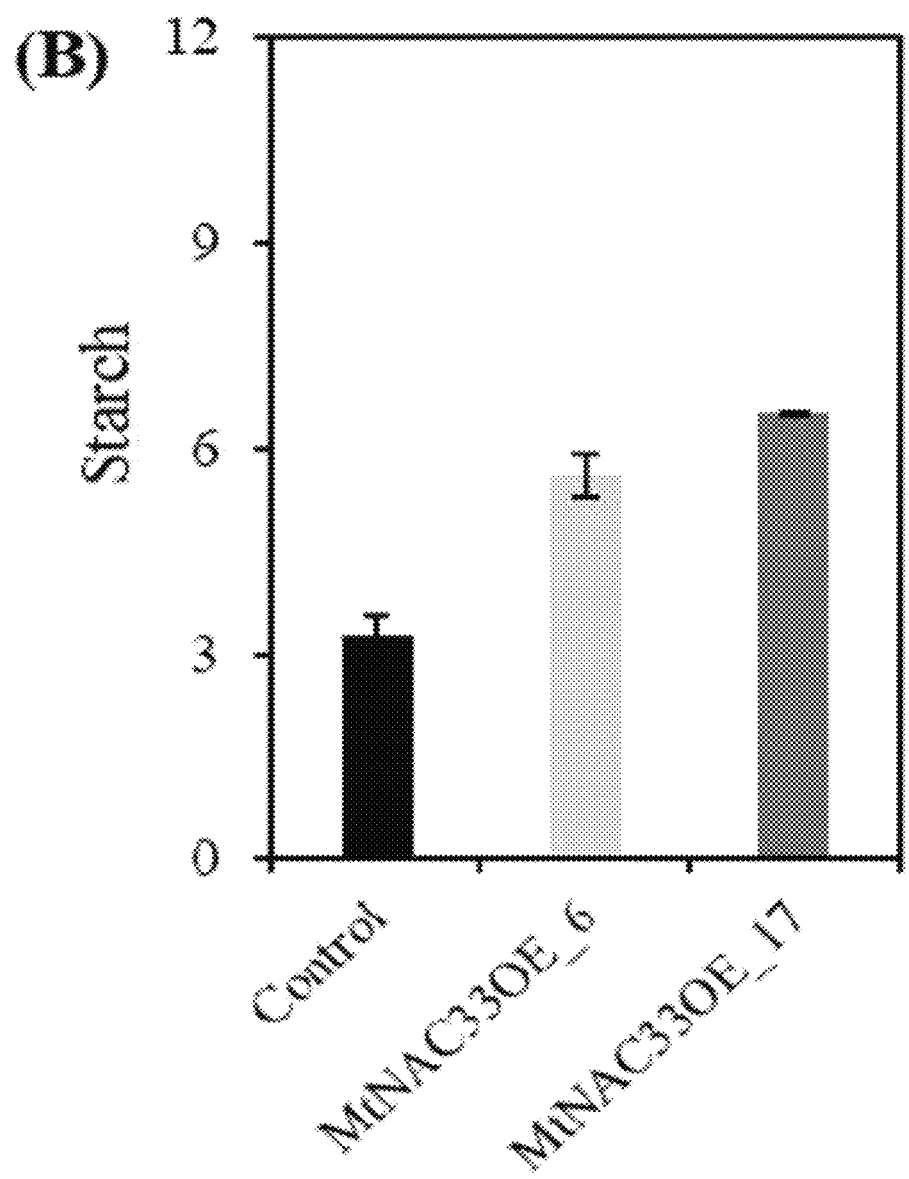
Figure 9C:
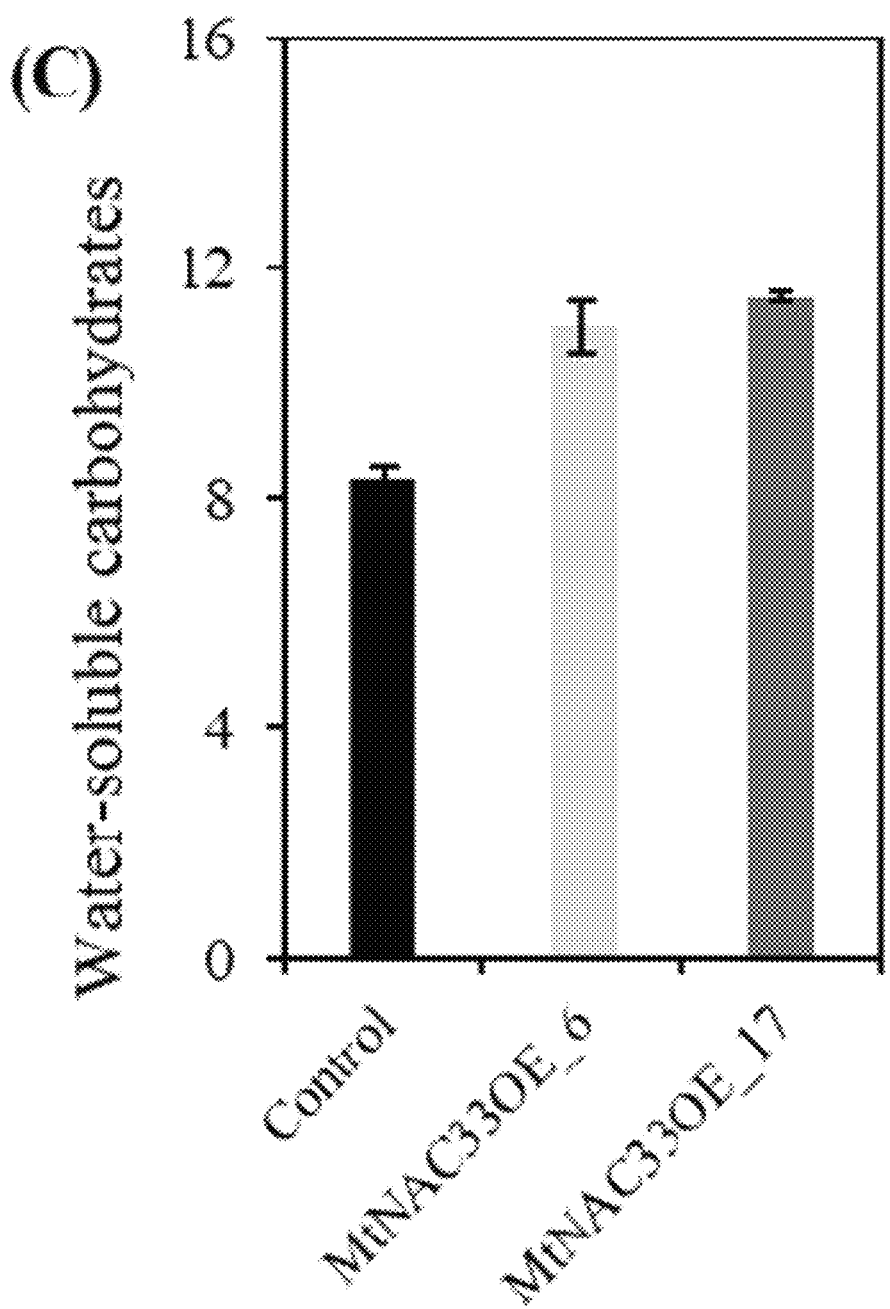
Figure 9D:
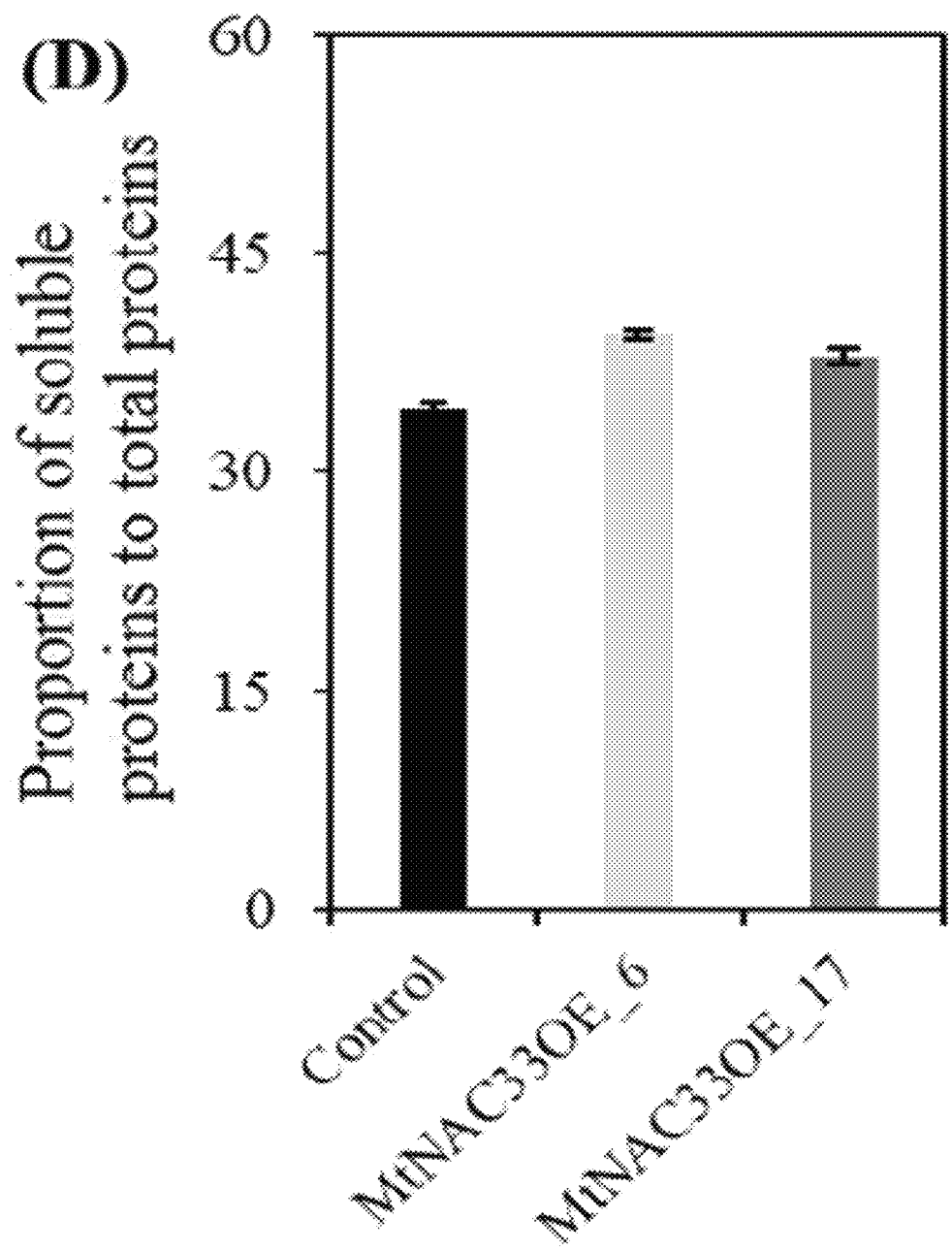

Example 5: Drought Tolerance of Over-Expressing MtNAC33 Transgenic Alfalfa Plants The transgenic plants (MtNAC33OE_6/17) with over-expression of MtNAC33 and significantly increased biomass in Example 4 and the control plants of Zhongmu No. 1 were subjected to rapid leaf water loss. The results showed that the photosynthesis of NAC33OE leaves was significant stronger than that of the control leaves after 48-hour and 72-hour exposed in the air (FIGS. 8A and B) (in the figure, darker color represents stronger photosynthetic capacity), while the leaves of Zhongmu NO. 1 had withered and lost the photosynthesis ability after 72-hour treatment (FIGS. 8A and 8B). In addition, after 15 days of drought stress, MtNAC33OE plants were still green and healthy while the control plants showed withered leaves (FIG. 8C). Following 15 days of drought exposure the plants were re-watered and grown under optimal moisture conditions for one week and then assessed for recovery. The control plants did not recover when re-watered, whereas MtNAC33OE recovered growth after drought stress (FIG. 8C). What's more, the scanning electron microscopy showed that the MtNAC33OE leaves had more closed stomata (FIG. 8D) and meanwhile smaller stomatal aperture (FIG. 8E) compared with those of the control plant leaves. Therefore, overexpression of MtNAC33 in alfalfa can significantly improve the drought tolerance of alfalfa.

Example 6: Forage Quality Determination of Over-Expressing MtNAC33 Transgenic Alfalfa Plants The early flowering shoots in Example 4 was tested using near-infrared scanning (Dairy One database) to measure the basic nutritional indicators of alfalfa, among which the monosaccharides, starch, water-soluble carbohydrates, and the proportion of soluble proteins to total proteins in the leaves of MtNAC33OE transgenic alfalfa had increased significantly (FIG. 9A-9D).

```
Gene MINAC33 (SEQ ID NO. 1):
ATGGCCGAAACAAAATTGATGATTCCAGGGTTTCGTTTTCACCCCACTG

ATGTTGAGCTGGTAATGTATTTTCTCAAGAGGAAGATTTTGGGTAGAAA

ATTCCCTTTTAATGTCATTGATGAACTTGACATTTACAAGTATGCTCCA

TGGGATCTACCAGAAAAATCTTTGCTCAAGAGTGGTGATTTGCAATGGT

ACTTCTTTACCCCTGTCGGAAAGAAATATTGCACGGGAGGGAGGATGAA

TCGGGCAACAGAAGTAGGCTACTGGAAGACTACAGGGAAGGATAGGTCG

ATTGAACATAGGAATCAAGTGGTGGGGATGATAAGAACCCTGGTGTTTC

ACACTGGCAAAGCTCCTAAAGGAGACCGAACTGATTGGGTTATGCATGA

TCCTATGTGATTTGTAGATACAGACTTGAAAACAAAGACCTAGCTGACA

ATGGTGTTCCACAGAACGGTATTTCAAAAGGAAGGTCCTGGTCCCAGGA

ATGGTGCACAGTATGGAAAACCATTTAATGAGAAAGACTGGGATAGCGA

AGAGGAAATTGATTATGTACAAGCTGTCCCTGTTGCTGCTGTGTCTGCA

CCAGCTCTCATTCTACCTAGCTCAAGCCATATTTCTGAAGAAAATGATA

TGCATACCTCTGCAAGGGGATGCACTGGACAGACCTCTTTATCAGGTCT

ATCAAGATTGATGCCCTCTGGCACGACACACCCTTCAGCTCCAGGCAAT

CAAGCTGATGATGACATTTTATCCATGCTTGCTATCTTTGACGATGAAA

ATGCATTGGCTGGGAATGAAAACAATGGATCTGAGAAGGTCGATAATCC

TGGTCAGGCAAACAATGCTGAAGATGTACCTTATTTAATTTCAAATGAG

ATTTTTGAGGACTTGGGAGATCTCAACAGCTTGGTTGGATTAGATGAAG

GAGGCGGTTTTTCCTATGGCCAAAAAGATGAGTACGAAAAGCTTTCTAC

TGGCAACGTCTCTTTGTTTTGCAACCCCCCTGATTTCTTTGAGTTGCTT

GACCTAGAGGTGCCATTATCTTGGCAGACTAAACATGATGGCTGA.

Protein MtNAC33 (SEQ ID NO. 2):
MAETKLMIPGFRFHPTDVELVMYFLKRKILGRKFPFNVIDELDIYKYAP

WDLPEKSLLKSGDLQWYFFTPVGKKYCTGGRMNRATEVGYWKTTGKDRS
```

-continued

IEHRNQVVGMIRTLVFHTGKAPKGDRTDWVMHEYRLENKDLADNGVPQN
SYVICRVFQKEGPGPRNGAQYGKPFNEKDWDSEEEIDYVQAVPVAAVSA
PALILPSSSHISEEENDMHTSARGCTGQTSLSGLSRLMPSGTTHPSAPGN

-continued

QADDDILSMLAIFDDENALAGNENNGSEKVDNPGQANNAEDVPYLISNE
IFEDLGDLNSLVGLDEGGGFSYGQKDEYEKLSTGNVSLFCNPPDFFELL
DLEVPLSWQTKHDG*

What is claimed is:

1. A method for improving biomass yield and drought tolerance of alfalfa, comprising the following steps:
   (1) constructing a pEG100-MtNAC33 vector;
   (2) introducing a MtNAC33 expression cassette comprising the pEG100-MtNAC33 vector into alfalfa by using an ultrasonic-assisted leaf disc transformation procedure mediated by an *Agrobacterium tumefaciens* strain EHA105; wherein the pEG100-MtNAC33 vector contains an MtNAC33 gene having the nucleotide sequence shown in SEQ ID NO: 1; and
   (3) conducting DL-Phosphinothricin resistance selection to obtain a positive transgenic alfalfa plant; wherein the positive transgenic plant shows delayed flowering time, increased leaf-to-stem ratio, improved dry biomass and increased drought tolerance.

2. A method for improving biomass yield and drought tolerance of alfalfa, comprising the following steps:
   (a) constructing a recombinant pEG100-MtNAC33 vector;
   (b) introducing a MtNAC33 expression cassette comprising the pEG100-MtNAC33 vector into alfalfa by using an ultrasonic-assisted leaf disc transformation procedure mediated by an *Agrobacterium tumefaciens* strain EHA105; wherein the pEG100-MtNAC33 vector contains an MtNAC33 gene having the nucleotide sequence shown in SEQ ID NO: 1;
   (c) expressing a protein encoded by the MtNAC33 gene in alfalfa, and the protein has the amino acid sequence set forth in SEQ ID NO: 2; and
   (d) conducting DL-Phosphinothricin resistance selection to obtain a positive transgenic alfalfa plant.

3. A method for improving biomass yield and drought tolerance of alfalfa, comprising the following steps:
   (i) constructing a pEG100-MtNAC33 vector;
   (ii) introducing the pEG100-MtNAC33 vector into alfalfa by using an ultrasonic-assisted leaf disc transformation procedure mediated by an *Agrobacterium tumefaciens* strain EHA105; wherein the pEG100-MtNAC33 vector contains an MtNAC33 gene having the nucleotide sequence shown in SEQ ID NO: 1; and
   (iii) conducting DL-Phosphinothricin resistance selection to obtain a positive transgenic alfalfa plant.

* * * * *